United States Patent [19]
Gao et al.

[11] Patent Number: 5,399,765
[45] Date of Patent: Mar. 21, 1995

[54] ENANTIOSELECTIVE PREPARATION OF OPTICALLY PURE ALBUTEROL

[75] Inventors: Yun Gao, Framingham; Charles M. Zepp, Berlin, both of Mass.

[73] Assignee: Sepracor, Inc., Marlborough, Mass.

[21] Appl. No.: 247,302

[22] Filed: May 23, 1994

[51] Int. Cl.⁶ .......................................... C07C 209/68
[52] U.S. Cl. .................................. 564/365; 560/42; 564/304; 564/356
[58] Field of Search ............... 560/42; 564/304, 356, 564/365

[56] References Cited

FOREIGN PATENT DOCUMENTS

WO92/04314  4/1992  WIPO .

OTHER PUBLICATIONS

Hartley et al. "Absolute Configuration of the Optical Isomers of Salbutamol" *J. Med. Chem.* 14, 895–896 (Apr. 17, 1971).

Hopkins "Salbutamol" *Drugs of the Future IV* 629–633 (May 2, 1979).

Floyd et al. "The Oxidation of Acetophenones to Arylglyoxals with Aqueous Hydrobromic Acid in Dimethyl Sulfoxide" *J. Org. Chem.* 50, 5022–5027 (Jun. 1, 1985).

Collin et al. "Saligenin Analogs of Sympathomimetic Catecholamines" Chemistry Dept., Allen and Hanburys Ltd. (Apr. 13, 1970).

*Primary Examiner*—Richard L. Raymond

[57] ABSTRACT

The invention relates to a method for producing albuterol by the resolution of a mixture of enantiomers of 5-[2-[(1,1-dimethylethyl)amino]-1-hydroxyethyl]-2-hydroxybenzoate using ditoluoyltartaric acid.

14 Claims, No Drawings

ENANTIOSELECTIVE PREPARATION OF OPTICALLY PURE ALBUTEROL

TECHNICAL FIELD

The present invention relates to a method of preparing optically pure (R) and (S) albuterol. More particularly, the present invention relates to the preparation and resolution of the albuterol precursor methyl 5-[2-[(1,1-dimethylethyl)amino]-1-hydroxyethyl]-2-hydroxybenzoate with a chiral acid.

BACKGROUND OF THE INVENTION

Albuterol, also referred to as α-[[(1,1-dimethylethyl)amino]methyl]-4-hydroxy-1,3-benzenedimethanol or salbutamol, is a β-2 agonist useful as a bronchodilator. It possesses a high degree of selectivity between β-1 receptors (which are present in the heart) and β-2 receptors (which are present in bronchial tissue and elsewhere), for which reason it is widely used in the treatment of asthma, since in therapeutic doses it exhibits fewer cardiac side effects than many other β-agonists.

It is known that among many drugs having chiral centers one enantiomer of a racemic pair is often more active than the other in treating a medical condition. Recent data suggest that the levorotatory R-isomer of albuterol is approximately 80 times more potent than the dextrorotatory S-isomer (Hartley and Middlemis, *J. Med. Chem.* 14 895–896 (1971)), and preliminary research indicates that administration of the pure R-enantiomer may offer an improved therapeutic ratio.

Methods of producing optically pure albuterol by resolving albuterol precursors are described only for precursors having the phenolic group protected as a benzyl ether. Hartley et al. op. cit. disclosed that optical resolutions of albuterol or any phenolic precursor were unsuccessful; resolution was possible only when the phenolic precursor was protected as a benzyl ether. The process described by Hartley required the use of expensive starting materials, involved at least 6 independent steps and produced low overall yields. Therefore, there exists a need for a more economical and efficient method of making optically pure albuterol.

SUMMARY OF THE INVENTION

It is an object of the invention to provide a method for obtaining an optically pure isomer of albuterol from a phenolic precursor.

It is a further object to provide a manipulatively simple synthesis of optically pure albuterol from a commercially available prochiral starting material in only four steps involving one highly efficient resolution.

This and other objects, features and advantages are provided by the present invention which relates to a process for obtaining a single enantiomer of 5-[2-[(1,1-dimethylethyl)amino]-1-hydroxyethyl]-2-hydroxybenzoate, a precursor to albuterol, comprising the steps of: (a) dissolving a mixture of enantiomers of methyl 5-[2-[(1,1-dimethylethyl)amino]-1-hydroxyethyl]-2-hydroxybenzoate and a chiral acid selected from the group consisting of (−)-di-toluoyl-L-tartaric acid and (+)-di-toluoyl-D-tartaric acid in methanol by heating to form a solution; (b) allowing said solution to cool, whereby a salt of primarily one stereoisomer crystallizes; (c) separating said salt from said solution; (d) recrystallizing said salt from methanol, whereby a diastereomeric salt having greater than 90% ee of an enantiomer of methyl 5-[2-[(1,1-dimethylethyl)amino]-1-hydroxyethyl]-2-hydroxybenzoate is obtained; (e) separating said diastereomeric salt from the methanol solvent; and (f) liberating said enantiomer of methyl 5-[2-[(1,1-dimethylethyl)amino]-1-hydroxyethyl]-2-hydroxybenzoate from said diastereomeric salt by treatment with base.

In the process described above, a chiral acid such as (−)-di-toluoyl-L-tartaric acid will give the S enantiomer of methyl 5-[2-[(1,1-dimethylethyl)amino]-1-hydroxyethyl]-2-hydroxybenzoate; (+)-di-toluoyl-D-tartaric acid will give the R enantiomer of methyl 5-[2-[(1,1-dimethylethyl)amino]-1-hydroxyethyl]-2-hydroxybenzoate.

In addition, the invention encompasses a process for making optically pure albuterol from a mixture of enantiomers of 5-[2-[(1,1-dimethylethyl)amino]-1-hydroxyethyl]-2-hydroxybenzoate. The process comprises steps (a) through (f) as described above, followed by reducing the enantiomer of methyl 5-[2-[(1,1-dimethylethyl)amino]-1-hydroxyethyl]-2-hydroxybenzoate thereby forming optically active albuterol. The reduction may be accomplished with either borane-methyl sulfide or lithium aluminum hydride.

In a specific aspect the invention relates to a method for producing optically pure albuterol from methyl 5-acetylsalicylate comprising the resolution and reduction described above in combination with a method for producing 5-[2-[(1,1-dimethylethyl)amino]-1-hydroxyethyl]-2-hydroxybenzoate. According to this aspect the methyl 5-[2-[(1,1-dimethylethyl)amino]-1-hydroxyethyl]-2-hydroxybenzoate is obtained by: (a) reacting methyl 5-acetylsalicylate with hydrogen bromide in dimethyl sulfoxide, thereby forming a keto aidehyde; (b) reacting said keto aldehyde with tertbutylamine, thereby forming an α-iminoketone; and (c) reducing said α-iminoketone to provide methyl 5-[2-[(1,1-dimethylethyl)amino]-1-hydroxyethyl]-2-hydroxybenzoate.

The α-iminoketone may be reduced with either a hydride reducing agent, such as sodium borohydride, sodium cyanoborohydride, or sodium triacetoxyborohydride or by catalytic hydrogenation with a heterogeneous noble-metal catalyst, such as Pd/C, Pt/C or PtO$_2$.

DETAILED DESCRIPTION

The present invention relates to a more economical and efficient process for making an optically pure albuterol. The method is particularly economical and efficient because it proceeds via readily available and inexpensive starting materials, as set forth in Scheme A below:

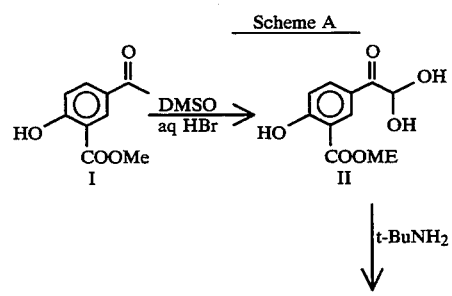

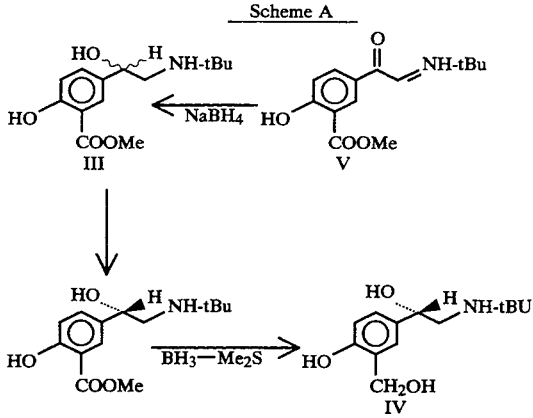

The graphic representations of racemic, ambiscalemic and scalemic or enantiomerically pure compounds used herein are taken from Mayer J. Chem. Ed. 62, 114–120 (1985). Thus, solid and broken wedges are used to denote the absolute configuration of a chiral element; wedge outlines and dotted or broken lines (e.g. IV) denote enantiomerically pure compounds of indeterminate absolute configuration. As usual, a wavy line indicates a mixture of enantiomers of indeterminate proportion, commonly a racemic mixture.

Many organic compounds exist in optically active forms, i.e., they have the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. There is no correlation between nomenclature for the absolute stereochemistry and for the rotation of an enantiomer. Thus, D-lactic acid is the same as (−) lactic acid, and L-lactic acid is (+). Compounds having a single chiral center exist as a pair of enantiomers which are identical except that they are non-superimposable mirror images of one another. A one-to-one mixture of enantiomers is often referred to as a racemic mixture.

The term "enantiomeric excess" is well known in the art and is defined for a resolution of ab→a+b as $$ee_a = \left( \frac{\text{conc. of } a - \text{conc. of } b}{\text{conc. of } a + \text{conc. of } b} \right) \times 100$$

The term "enantiomeric excess" is related to the older term "optical purity" in that both are measures of the same phenomenon. The value of ee will be a number from 0 to 100, 0 being racemic and 100 being pure, single enantiomer. A compound which in the past might have been called 98% optically pure is now more precisely described as 96% ee. Processes that yield products of ee less than about 80% are not generally regarded as commercially attractive. Processes that yield albuterol of ee greater than about 96% are particularly attractive because the eutectic of albuterol is about 96–97% and thus substantially pure single enantiomers can be obtained by simple recrystallization of the product.

Arylglyoxals (II) are most conveniently prepared from acetophenone derivatives by the procedure of U.S. Pat. No. 5,283,359, although other syntheses, well known to persons skilled in the art, are also suitable.

The starting material shown in Scheme A above, methyl 5-acetylsalicylate, is commercially available. Oxidation in DMSO (1.0 M) in the presence of 2 equivalents of aqueous HBr proceeds smoothly at 60° C. over 20 hours to give the arylglyoxal II in greater than 80% yield. However, prolonged reaction times and temperatures exceeding 70° C. may result in lower yields. Without further purification, this compound is treated with 1.0–1.2 eq of t-butylamine in warm toluene or ethyl acetate to give the α-iminoketone V in greater than 70% yield. The α-iminoketone can be further purified by recrystallization from toluene/heptane and is used in the reduction after drying. The overall yield from the salicylate is greater than 60%.

The α-iminoketone V is dissolved in a suitable solvent such as methanol and cooled with ice water. Approximately 2.5 equivalents of a hydride reducing agent are added in portions and the mixture is stirred at room temperature overnight. Thereafter the mixture is concentrated, quenched with water, and extracted into a suitable solvent, washed and recrystallized from ethyl acetate-heptane in overall yield of about 78%. The product may be analyzed for purity by any one of many methods well known in the art, an example being HPLC analysis. If the solid amino-alcohol of formula III is not greater than 95 area % pure by HPLC analysis, recrystallization is preferably repeated until this level of purity is met prior to use of the same in the resolution step.

Alternatively, the compound of formula III may also be prepared directly from the corresponding α-iminoketone V by the catalytic reductive amination with t-butylamine in the presence of heterogeneous noble-metal catalysts such as Pd/C, Pt/C or PtO₂.

The precursor III is resolved with a chiral acid such as (−) or (+) di-p-toluoyltartaric acid. This may be accomplished by dissolving the phenolic precursor III and the chiral acid in refluxing methanol. Although this solvent may alternatively comprise ethanol or a methanol/ethanol mixture, methanol is the preferred solvent. The methanol solution is then cooled and stirred at 20°–25° C. for 3 to 20 hours, preferably 2 to 3 hours, thereby forming a tartrate salt in the form of a white solid. The salt is filtered off, washed with ethyl acetate to remove impurities and then dried. At this point the diastereomeric salt may represent approximately a 50% yield, of 93% ee. The solid is preferably dissolved again in refluxing methanol and the resulting solution cooled to room temperature and stored at 0° to 5° C. for 10 to 20 hours. The white solid is again collected by means known in the art, such as by filtration, and dried to produce a diastereomeric salt of approximately 98.5% ee, from which the product 5-[2-[(1,1-dimethylethyl)amino]-1-hydroxyethyl]-2-hydroxybenzoate may be obtained by treatment with base, extraction, and, if desired, recrystallization from ethyl acetate.

The salicylic ester III is reduced to substantially optically pure albuterol by treatment with 2 to 3 equivalents of borane-methyl sulfide complex (BH₃.Me₂S) in a suitable solvent, such as dichloromethane or toluene at temperatures from 50° to 60° C. It is preferred that the reaction is not heated over 60° C. since higher temperatures may result in overreduction of the product. In addition, these steps are preferably performed under a dry nitrogen or argon atmosphere and the reactants and products protected from light. The reaction is quenched with methanol and worked up as usual in the art.

The highly efficient synthesis shown in Scheme A is made possible by the surprising discovery that the free phenol of formula III can be resolved in good yield in a single recrystallization employing a relatively inexpensive chiral acid. Previous syntheses required either more expensive starting materials or additional protection and deprotection steps, because arriving at unresolved III was considered a synthetic dead end.

EXAMPLE 1

The synthesis of the keto aldehyde hydrate II was performed using a 500 mL three neck flask charged with 150 mL of dimethyl sulfoxide (DMSO) and methyl 5-acetylsalicylate (I) (39 g, 0.2 mol). Aq. HBr (48%, 6 mL, 0.4 mol. 2.0 eq) was added dropwise over 30 min. After addition, the solution was heated at 60°–70° C. for ca. 20 hours (followed by TLC) until no starting material remained. The yellow mixture was poured onto 400 g of ice, stirred for 30 minutes, collected by filtration, and washed with 2×50 mL of cold water to give the keto aldehyde hydrate (II) (yield >80% based on dried material). The wet solid was dried at room temperature under vacuum for 4 hours and used for the next step without further purification.

The wet solid (1.0 eq, based on 0.2 mol, 100% yield) and 1.1 eq of t-butylamine (0.22 mol, 23 mL) were dissolved in 200 mL of toluene. The solution was heated at reflux for ca. 2 hours. The solution was then cooled to room temperature and washed with water (2×50 mL) and concentrated to dryness under vacuum to give crude ketoimine V as yellow solid (33.4 g, 63% yield from methyl 5-acetylsalicylate). The crude ketoimine can be further purified for use in the NaBH4 reduction. In this case, it was reduced directly with NaBH4 in methanol (MeOH).

The crude ketoimine (10.6 g, 25 mmol) was dissolved in 100 mL of MeOH and cooled with icewater. Solid NaBH4 (2.5 g, 62.5 mmol, 2.5 eq) was added in portions with caution due to hydrogen evolution. The resulting mixture was stirred at room temperature overnight (TLC: completed) and then concentrated to dryness. The residue was quenched with 20 mL of water and extracted with 2×150 mL of ethyl acetate. The ethyl acetate solution was washed with 25 mL of NaHCO3 and 25 mL of water. The solution was then concentrated to ca. 40 mL to give a slurry. The slurry was heated to dissolve the solid, and heptane (ca. 30 mL) was added. The solution was cooled to room temperature, and then stored at 3° C. overnight. The solid was collected by filtration to give the first crop. The mother liquor was concentrated and recrystallized to give a second crop. Total recovery of the phenolic solid was 6.9 g (78% yield) as white solid.

EXAMPLE 2

Resolution of the phenolic precursor III was performed with (−)-di-p-toluoyl-L-tartaric acid and (+)-di-p-toluoyl-D-tartaric acid, respectively.

In a representative case (examples 2.4 and 2.4a), a mixture of the phenolic precursor III (1.33 g, 5 mmol) and (+)-di-p-toluoyl-D-tartaric acid (1.93 g, 5 mmol) was dissolved in refluxing MeOH (40 mL). The solution was then cooled and stirred at room temperature for 16 hours. The white solid was collected by filtration and washed with 5 mL of ethyl acetate and dried (0.86 g, 53% yield, 93% ee). The solid was then dissolved again in 18 mL of refluxing MeOH. The resulting solution was cooled to room temperature and stored at 3° C. for 15 hours (overnight). The white solid was collected by filtration and dried (0.53 g, 33% yield, 98.5% ee). Results obtained analogously are summarized in the following table:

| Example | Chiral acid | Solvent | Time at Room Temperature | Time at 3° C. | ee % of solid | Yield % of solid | ee % of ML |
|---|---|---|---|---|---|---|---|
| 2.1 | (−)-L | EtOAc/MeOH | 15 | 1.5 | 90 (S) | 50 | 27 |
| 2.2 | (+)-D | EtOAc/MeOH | 15 | 1.5 | 77 (R) | 66 | 45 |
| 2.3 | (+)-D | EtOH/MeOH | 6 | | 75 (R) | 75 | — |
| 2.3a | — | MeOH | 2 | 15 | 95 (R) | 45 | — |
| 2.3b | — | MeOH | 3 | 15 | 98 (R) | 31 | — |
| 2.4 | (+)-D | MeOH | 16 | | 93 (R) | 53 | — |
| 2.4a | — | MeOH | 3 | 15 | 99 (R) | 33 | — |
| 2.5 | (+)-D | MeOH | 3 | 15 | 90 (R) | 54 | 38 (S) |
| 2.5a | — | MeOH | 3 | 15 | 99 (R) | 33 | — |

Examples identified as a or b indicate the results of an additional recrystallization of the solid obtained from the preceding crystallization. The optically pure tartrate salt can be obtained after just one more recrystallization in over 30% yield based on available isomer.

The absolute configuration of the salt from resolution with (+)-di-p-toluoyl-D-tartaric acid was correlated to R-albuterol according to the following procedure: a small amount of the salt was neutralized with saturated aqueous NaHCO3 in the presence of ethyl acetate. The ethyl acetate phase was concentrated to dryness to give the enriched free base material of formula III which was then reduced with BH3.Me2S in CH2Cl2 to give optically active albuterol. HPLC analysis in comparison with authentic (R)-albuterol confirmed that the salt has (R)-configuration at the benzyl OH group.

EXAMPLE 3

A 500 mL three-necked flask equipped with a mechanical stirrer was charged with 200 mL of DMSO (99%, ACS reagent grade) and methyl 5-acetylsalicylate (97.7% Schweizerhall, 39.6 g, 0.2 mol, 1.0 eq). Aqueous hydrobromic acid (48% ACS reagent grade, 34 mL, 0.3 mol, 1.5 eq) was added dropwise with stirring over 15–20 minutes. The solution was then heated at 60°–65° C. for 24–26 hours with stirring. Refluxing of the solution occurred at ca. 60° C. The reaction was followed by HPLC and heating was stopped when the ratio of product to starting material was greater than 95:5 by area HPLC. A μBondapak C18, 10 μm, 30 cm×3.9 mm (Waters) column with a mobile phase consisting of 0.01 M $Na_2H_2PO_4$—0.002 M Octanesulfonic acid, sodium salt (pH 3.0)/Acetonitrile (75:25) was used to monitor the reaction at a UV detection wavelength of 220 nm. Prolonged reaction times and higher temperatures (over 70° C.) resulted in lower yield. The solution was slowly poured onto 500 g of ice with vigorous stirring. A yellow solid precipitated out of the solution with some sticky solids being present. The mixture was stirred at 10° C. for 2 hours until a fine slurry was formed during which time most of the sticky solid changed to a fine powder or small pieces. The slurry was filtered through a Buchner funnel using filter paper or DMSO-compatible filter cloth to recover the arylglyoxal product of formula II in the form of a yellow powder. The flask and solids were washed twice with 50 mL of cold water (5° C.) followed by dual washes with 15 mL of cold toluene (5°–10° C.). The powder was retrieved and held under a vacuum for ca. 1 hour which removed most of the solvent, no additional drying was required. The powder was used without further purification having a crude yield of ca. 80% when dry with the average weight of the arylglyoxal solid falling in the range of 55–65 g.

The arylglyoxal solid (the 55–65 g., 0.2 mol) obtained from the preceding process was then transferred to a second 500 mL three-necked flask charged with 300 mL of ethyl acetate (99%, ACS reagent) thereby forming a yellow slurry. The amount of crude arylglyoxal was based on 100% yield on step one. Tertiary-butylamine (98%, Aldrich, 31.4 mL, 0.3 mol, 1.5 eq) was added to the slurry over 15–20 minutes with stirring, thereby dissolving the solids within the slurry and forming an orange solution. The mixture was heated at 40°–45° C. for 2–3 hours. The reaction was followed by TLC (silica gel plate pretreated with 10:1 (v/v) hexane: Et3N; eluting with $CH_2Cl_2$:MeOH (20:1, v/v) containing 2 volume % of $EtN_3$), $R_f$ starting material: 0.55, ketoimine: 0.68; UV). The reaction was worked up when the starting material was almost invisible by UV detection. The solution was cooled to 20°–25° C. (room temperature) and separated from the dark aqueous phase. The organic phase was washed twice with 30 mL of saturated aqueous sodium chloride solution. The combined aqueous phase was not extracted and the amount of ketoimine product in the aqueous phase was ca. 5–6% of the overall yield. The organic phase was then concentrated to dryness and further dried under vacuum for 2–3 hours at room temperature yielding a yellow solid of crude ketoimine of formula V (31–35 g, 75–82% crude yield). The crude product was used without further drying and purification in the reduction step set forth below.

A 500 mL three-necked flask was charged with the crude ketoimine from above (32 g, 0.122 mol, 1.0 eq) and 300 mL of methanol (99% ACS reagent grade) and cooled to 10°–15° C. Sodium borohydride ($NaBH_4$) (98%, reagent grade) (11.6 g, 0.31 mol, 2.5 eq) was dissolved in 50 mL of 0.2% sodium hydroxide solution and added to the ketoimine solution at 10°–20° C. with vigorous stirring over 30–40 minutes. This is an exothermic reaction and $H_2$ is released during addition, both of which may be controlled by using a cooling bath and by controlling the rate of addition. A slurry was formed during addition which was then stirred at 10°–15° C. for 20–30 minutes. The reaction usually completes after addition of the $NaBH_4$. The reaction was followed by TLC (silica gel, mobile phase:2 v/v % $Et_3N$ in 20:1 $CH_2Cl_2$/MeOH; UV, $R_f$: ketoimine, 0.44; product, 0.29) or HPLC as described hereinabove. The reaction was worked up when no arylglyoxal starting material was detected by TLC or HPLC. The slurry was concentrated below 35° C. under vacuum to ca. 100–120 mL thereby forming a dense slurry. 800 mL of ethyl acetate and 150 mL of distilled water were added to the dense slurry, stirred at 20°–25° C. for 30–40 minutes and allowed to settle. Although some solid slurry was present in the aqueous phase it did not affect phase separation. After separating out the aqueous phase the organic phase was washed with 50 mL of distilled water, then 50 mL of saturated NaCL solution. The organic phase was concentrated to dryness yielding a yellowish solid, weighing ca. 20–35 g. greater than 95 area % pure by HPLC. The crude product was dissolved in 150–200 mL of ethyl acetate under refluxing. Thereafter, 50 mL of heptane was added to the hot solution. The weight/volume ratio of crude product to ethyl acetate is ca. 0.2:1. The volume ratio of ethyl acetate to heptane is 3:1. Although solids started to form at 40° C. the mixture was stirred and cooled to 20°–25° C. over 2 hours and then at 0°–5° C. for 4 hours. The mixture was filtered to recover the product and the flask and solids washed with 50 mL of ethyl acetate/heptane (1:1, v/v) and dried under vacuum thereby forming a white solid (33 g., 78.5% yield, 97.7 area % by HPLC). The white solid was a racemic amino-alcohol of formula III. Typically the yield after recrystallization is in the range of 55–70% and more product can be recovered from the filtrate. The product was analyzed by HPLC and should be greater than 95 area % pure for use in the resolution step and, if not, then recrystallization should be repeated.

A 500 mL three-necked flask was charged with 304 mL of methanol and (+)-di-p-toluoyl-D-tartaric acid or its monohydrate (greater than 98%) (30.6 g., 76 mmol, 1.0 eq) and heated to 60°–65° C. with the stirring. The racemic amino-alcohol (20.0 g., 76 mmol, 1.0 eq) was added in one portion to the heated solution with stirring. The heating is necessary for the formation of the salt and the production of a homogeneous solution. The solution was then cooled to room temperature over about 1.5 hours and held at room temperature (22° C.) for 4 hours, then at 0° C. for 1–2 hours with stirring. It is preferred that the mixture is not cooled below 0° C. The solid formed was recovered by filtration and the flask and cake rinsed with ca. 30 mL of ethyl acetate. The recovered solid was then dried under vacuum to give (21.2 g) of a white solid as the tartrate salt (80% ee in favor of the R-isomer, 42.7% yield or 85.4% yield based on available isomer). The ee was determined by HPLC on the free base, which was formed after neutralization with 5 weight % $Na_2CO_3$ in the presence of ethyl acetate. HPLC for optical purity may be conducted using a sumichiral OA 4900, 5μ, 4.6×250 mm column and a mobile phase of 240(hexane):140(dichloromethane):20(methanol): 1(trifluoacetic acid) and a UV detection wavelength of 280 nm. The ee of the mother liquor was 69.3% in favor of the S-isomer. The tartrate salt was dissolved in 374 mL of methanol at reflux. The concentration of the salt in methanol was about 5.7% w/v (the range of salt concentration is 5.5–6.0% w/v in methanol). The solution was cooled to room temperature (22° C.) over 1.5 hours with stirring and then stirred at room temperature for an additional 4–5 hours. The solution was further cooled to a temperature of 0° C. for 1–2 hours. The solids were collected by filtration and washed with 25 mL of ethyl acetate and dried at 40° C. at 28 inches of Hg for 2 hours to give the enriched tartrate salt (14.0 g, 99.1% ee of the R-isomer, 56% yield based on available isomer). The enriched salt was greater than 90% area pure by HPLC. Additional enriched salt was recovered from the filtrate by concentrating it to dryness and dissolving the residue in methanol at reflux to make a 5.0-5.5% w/v solution which was cooled to room temperature over 1.5-2 hours and stirred at room temperature for 3-4 hours at 0° C. for 1 hour. The solids were recovered as above to give an enriched salt in 14% yield greater than 98% ee. The solids were combined and transferred to a flask to which 375 mL of ethyl acetate was added thereby forming a slurry. 91.2 mL of $Na_2CO_3$ solution (5 weight % aqueous solution) was added to the slurry with stirring at room temperature (22°-25° C.) for 30 minutes. The amount of $Na_2CO_3$ solution used represents two equivalents of $Na_2CO_3$ for each equivalent of tartrate salt. The pH of the aqueous solution is preferably ca. 9-10 (pH paper or pH meter), if the pH is less than 9, more sodium carbonate should be added to the solution to obtain the preferred pH.

The solution was then heated to ca. 30° C. and the aqueous phase separated out. The organic phase was washed with 40 mL of $Na_2CO_3$ solution (5 weight %) and 28 mL of saturated NaCl solution. The solution was kept at ca. 30° C. to prevent the free amino alcohol from crystallizing out from the ethyl acetate solution. The removal of the di-toluoyl-D-tartaric acid by sodium carbonate extraction was followed by the HPLC method described hereinabove. The amount of tartaric acid left should be 0% area by HPLC and if it exceeds this amount, the organic phase is preferably washed again with a sodium carbonate solution. The organic phase was dried with 10 g of anhydrous $Na_2SO_4$, and the organic solution concentrated to dryness which gave the free base as a white solid. The white solids were dissolved in 65 mL of ethyl acetate under reflux and thereafter cooled to room temperature over 1 hour with stirring. The solution remained at room temperature (22°-25° C.) with stirring for 1 hour and then at 0° C. for 2-3 hours. The white solid formed was recovered by filtration and dried at 40° C. (28 inches of Hg) for 2 hours to give an enriched R-amino-alcohol (5.0 g, 87.7% yield, greater than 99% ee, chemical purity greater than 99% area).

The R-amino-alcohol (2.67 g, 10 mmol, 1.0 eq) was added to a 100 mL flame-dried three-necked flask previously charged with 20 mL of ethylene glycol dimethyl ether (DME) (anhydrous, water less than 0.005%, 99+%). This reaction and all subsequent operations were performed under dry nitrogen or argon and the reaction solutions and final products protected from light. Borane dimethyl sulfide complex ($BH_3Me_2S$) (10 M, aldrich grade) (1.6 mL, 16 mmol, 1.6 eq) was added dropwise to the above slurry over 5 minutes with stirring. Hydrogen is released and the reaction slightly exothermic (from 25° C. to ca. 30° C.). The solution is then heated at ca. 55° C. for 3 hours. The reaction is followed by HPLC and if after 3 hours of reaction starting material is still greater than 0.3% area, it is preferred that an additional 0.1 eq of $BH_3.Me_2S$ be added and the solution heated at ca. 55° C. for an additional hour. It is preferred that the reaction is not heated over 60° C. since higher temperatures may result in overreduction of the product. Once the reaction has progressed to the desired point heating was stopped and the solution cooled to 5°-10° C. with use of an ice water bath. 40 mL of methanol was heated at reflux for 1 hour to destroy excess borane by forming trimethyl borane, freeing the albuterol product. 40 mL of solvent was distilled out at 60°-66° C./1 atm and then an additional 20 mL of methanol was added. Another 20 mL of the solvent was distilled out at 60°-66°/1 atm. The methylborate was removed azeotropically with methanol at 60°-66° C. 70 mL of DME was then added followed by distilling out the solvent until the temperature reached 85° C. An additional ca. 10 mL of DME was added at 80°-85° C. to maintain the solvent volume at 40-45 mL during distillation. The leftover methanol was removed azeotropically with the DME. The additional DME was added slowly at reflux to prevent precipitation of solids. The final solvent volume is preferably ca. 40-45 mL. The solution was checked by HPLC: the boron-complex ($t_{Ro}$ 17.0 minutes) should be less than 0.4% area on HPLC otherwise additional DME should be added and distillation continued. Then 25 mL of cyclohexane was added slowly over 10 minutes, to prevent oil-out, at ca. 80° C. Heating was then stopped and the solution cooled to ca. 20°-25° C. (room temperature) over 1 hour and then to 0°-5° C. over 1 hour and maintained at this temperature for an additional 3 hours with stirring. The solution was cooled slowly to prevent oil-out. The white powder formed was recovered by filtration. The flask and solids underwent dual washings with 10 mL of cyclohexane, the solids were dried at 50°-60° C./28 inches of Hg for over 12 hours. This yielded a white powder, (R)-albuterol of formula IV (weight 1.9 g, 80% yield, 98.4% area, 98% ee).

While the invention has been particularly shown and described with reference to preferred embodiments thereof, it will be understood by those skilled in the art that other changes in form and details may be made therein without departing from the spirit and scope of the invention.

What is claimed is:

1. A method for obtaining a single enantiomer of methyl 5-[2-[(1,1-dimethylethyl)amino]-1-hydroxyethyl]-2-hydroxybenzoate comprising the steps of:
   (a) dissolving a mixture of enantiomers of methyl 5-[2-[(1,1-dimethylethyl)amino]-1-hydroxyethyl]-2-hydroxybenzoate and a chiral acid selected from the group consisting of (−)-di-toluoyl-L-tartaric acid and (+)-di-toluoyl-D-tartaric acid in methanol by heating to form a solution;
   (b) allowing said solution to cool, whereby a salt of primarily one stereoisomer crystallizes;
   (c) separating said salt from said solution;
   (d) recrystallizing said salt from methanol, whereby a diastereomeric salt having greater than 90% ee of an enantiomer of methyl 5-[2-[(1,1-dimethylethyl)amino]-1-hydroxyethyl]-2-hydroxybenzoate is obtained
   (e) separating said diastereomeric salt from the methanol solvent; and
   (f) liberating said enantiomer of methyl 5-[2-[(1,1-dimethylethyl)amino]-1-hydroxyethyl]-2-hydroxybenzoate from said diastereomeric salt by treatment with base.

2. A method according to claim 1 wherein said chiral acid is (−)-di-toluoyl-L-tartaric acid and said enantiomer of methyl 5-[2-[(1,1-dimethylethyl)amino]-1-hydroxyethyl]-2-hydroxybenzoate is the S enantiomer.

3. A method according to claim 1 wherein said chiral acid is (+)-di-toluoyl-D-tartaric acid and said enantiomer of methyl 5-[2-[(1,1-dimethylethyl)amino]-1-hydroxyethyl]-2-hydroxybenzoate is the R enantiomer.

4. A method for making optically pure albuterol comprising the steps of:
   (a) dissolving a mixture of enantiomers of methyl 5-[2-[(1,1-dimethylethyl)amino]-1-hydroxyethyl]-2-hydroxybenzoate and a chiral acid selected from the group consisting of (−)-di-toluoyl-L-tartaric acid and (+)-di-toluoyl-D-tartaric acid in methanol by heating to form a solution;
   (b) allowing said solution to cool, whereby a salt of primarily one stereoisomer crystallizes;
   (c) separating said salt from said solution;
   (d) recrystallizing said salt from methanol, whereby a diastereomeric salt having greater than 90% ee of an enantiomer of methyl 5-[2-[(1,1-dimethylethyl)amino]-1-hydroxyethyl]-2-hydroxybenzoate is obtained;
   (e) separating said diastereomeric salt from the methanol solvent;
   (f) liberating the enantiomer of methyl 5-[2-[(1,1-dimethylethyl)amino]-1-hydroxyethyl]-2-hydroxybenzoate from said diastereomeric salt by treatment with base; and
   (g) reducing said enantiomer of methyl 5-[2-[(1,1-dimethylethyl)amino]-1-hydroxyethyl]-2-hydroxybenzoate thereby forming optically active albuterol.

5. The method of claim 4 wherein said enantiomer of 5-[2-[(1,1-dimethylethyl)amino]-1-hydroxyethyl]-2-hydroxybenzoate is reduced with borane-methyl sulfide.

6. The method of claim 4 wherein said enantiomer of 5-[2-[(1,1-dimethylethyl)amino]-1-hydroxyethyl]-2-hydroxybenzoate is reduced with lithium aluminum hydride.

7. The method of claim 4 wherein said mixture of enantiomers of methyl 5-[2-[(1,1-dimethylethyl)amino]-1-hydroxyethyl]-2-hydroxybenzoate is obtained by the steps of:
   (a) reacting methyl 5-acetylsalicylate with hydrogen bromide in dimethyl sulfoxide, thereby forming a keto aldehyde;
   (b) reacting said keto aldehyde with tert butylamine, thereby forming an α-iminoketone; and
   (c) reducing said α-iminoketone to provide methyl 5-[2-[(1,1-dimethylethyl)amino]-1-hydroxyethyl]-2-hydroxybenzoate.

8. A method according to claim 7 wherein said α-iminoketone is reduced with a hydride reducing agent.

9. The method of claim 7 wherein said hydride reducing agent is selected from the group consisting of sodium borohydride, sodium cyanoborohydride, and sodium triacetoxyborohydride.

10. A method according to claim 7 wherein said α-iminoketone is reduced by catalytic hydrogenation.

11. A method according to claim 10 wherein said catalytic hydrogenation is carried out over a heterogeneous noble-metal catalyst.

12. The method of claim 11 wherein said heterogeneous noble-metal catalyst is Pd/C.

13. The method of claim 11 wherein said heterogeneous noble-metal catalyst is Pt/C.

14. The method of claim 11 wherein said heterogeneous noble-metal catalyst is $PtO_2$.

* * * * *